United States Patent [19]

Bohn et al.

[11] 4,302,385
[45] Nov. 24, 1981

[54] PLACENTA-SPECIFIC TISSUE PROTEIN $PP_{10}$

[75] Inventors: Hans Bohn, Marburg an der Lahn; Walter Kraus, Bürgeln, both of Fed. Rep. of Germany

[73] Assignee: Behringwerke Aktiengesellschaft, Marburg an der Lahn, Fed. Rep. of Germany

[21] Appl. No.: 104,119

[22] Filed: Dec. 17, 1979

[30] Foreign Application Priority Data

Dec. 19, 1978 [DE] Fed. Rep. of Germany ....... 2854759

[51] Int. Cl.³ .................. A61K 35/50; A61K 39/395; C07G/7/00

[52] U.S. Cl. .............................. 260/112 B; 260/112 R; 424/85; 424/88; 424/12;

[58] Field of Search ................. 260/112 R, 112 B; 424/85, 88, 12

[56] References Cited

U.S. PATENT DOCUMENTS 3,904,751 9/1975 Zwister et al. ................... 424/105
4,041,021 9/1977 Bohn .................................. 260/112 B
4,065,445 12/1977 Bohn et al. ....................... 260/112 B
4,217,339 8/1980 Bohn et al. ..................... 260/112 B X
4,254,021 3/1981 Bohn et al. ...................... 260/112 R

OTHER PUBLICATIONS

Arch. Gynäkologie 222, 5-13 (1977), Bohn et al.
Arch. Gynäkologie 215, 263-275 (1973), Bohn.
Arch. Gynäkologie 221, 73-81 (1976), Bohn et al.
Chem. Abstracts, vol. 86, 1977, 135224x, Bohn et al.
Chem. Abstracts, vol. 55, 23,724f (1961), Centonze et al.
Chem. Abstracts, vol. 80, 1974, 79744d, Bohn.
Chem. Abstracts, vol. 77, 1972, 162901m, Bohn.
Chem. Abstracts, vol. 90, 1979, 68206k, Bohn et al., effective date 11/16/78.
Chem. Abstracts, vol. 85, 1976, 88842q, Bohn et al.

Primary Examiner—Howard E. Schain
Attorney, Agent, or Firm—Curtis, Morris & Safford

[57] ABSTRACT

A new placenta-specific protein ($PP_{10}$) and a process for isolating it are described.

3 Claims, No Drawings

PLACENTA-SPECIFIC TISSUE PROTEIN PP₁₀

The invention relates to a new placenta-specific protein ($PP_{10}$) and to its isolation from placentas.

Thus, the object of the invention is the placenta-specific protein $PP_{10}$, which is characterized by (a) a protein proportion of $93\pm3\%$, a content of carbohydrates of $6.65\pm1.55\%$, and thereof hexoses $4.8\pm1.0\%$, hexosamines $1.2\pm0.3\%$, fucose $0.05\pm0.05\%$, sialic acid $0.6\pm0.2\%$;

(b) a sedimentation coefficient $S_{20/w}°$, of $3.8\pm0.2$ S;

(c) a molecular weight determined in the ultracentrifuge of $48\,000\pm5\,000$;

(d) a molecular weight determined in sodium dodecyl sulfate (SDS)-containing polyacrylamide gel of $65\,000\pm5\,000$;

(e) an extinction coefficient $E_{1\ cm}^{1\%}$ (280 nm) of $10.9\pm0.5$;

(f) an electrophoretic mobility in the range of $\alpha_1$-globulins;

(g) an isoelectric point of $5.1\pm0.3$.

The following explanations serve to illustrate the characteristics of the new tissue protein:

Determination of the sedimentation coefficient was effected in an analytical ultracentrifuge of Messrs. Beckmann (Spinco-apparatus, model E) at 60,0000 Rpm in double sector cells with the aid of UV-scanner-technique at 280 nm. The solvent was a 0.05 M phosphate buffer (pH 6.8) containing 0.2 moles/l of NaCl. The protein concentration was adjusted to about 3 O.D. (O.D.=Optical density). The sedimentation coefficients were calculated on the basis of water having a temperature of 20° C.

For determining the molecular weight in the ultracentrifuge, the sedimentation equilibrium method was used. The concentration of the protein was adjusted for this purpose to about 1.0 O.D. The determination was effected at 9,000 Rpm. Registration was carried out with an UV-optical lens at 280 nm using a photoelectric scanner.

For determining the molecular weight in SDS-PAA-gel, a gel with 7.5% of polyacrylamide containing 0.1% of sodium dodecyl sulfate (SDS) was used. As comparative substances, human placenta lactogen (HPL) and human albumin as well as the aggregates thereof were used.

In order to determine the extinction coefficient, the substance was dissolved in distilled water to a strength of 0.10%.

The determination of the electrophoretic mobility was effected by the micro-modification test using the apparatus Microzone R 200 of Beckmann Instruments, on cellulose acetate foils (Messrs. Sartorius) and sodium diethyl barbiturate buffer, pH 8.6.

The determination of the isoelectric point was carried out on a column (440 m) of Messrs. LKB, Stockholm. The so-called ampholine-mixture used for the investigation had a pH-range of from 4.0 to 6.0.

Determination of carbohydrates was effected according to the method described by H. E. Schultze, R. Schmidtberger, H. Haupt, Biochem., Z., 329, page 490 (1958).

The analysis for amino-acids was effected according to S. Moore, D. H. Spackmann, W. H. Stein, Anal. Chem. 30, page 1185 (1958) using the liquid chromatograph Multichrom B of Messrs. Beckmann. ½-Cysteine was determined, after oxidation of the proteins, with performic acid (S. Moore et al., Anal. Chem. 30, page 1185, (1958) and following chromatography (S. Moore, J. Biol. Chem., 238, page 235 (1963) as cysteinic acid. The tryptophan content was determined by the direct photometric determination test according to H. Edelhoch, Biochemistry, 6, page 1948 (1967).

The results of the analysis for amino-acids of the $PP_{10}$ obtained according to the Example are compiled in Table I.

TABLE I

| | Composition of amino-acids of $PP_{10}$ (Radicals per 100 radicals) Mole % | |
|---|---|---|
| | | Variation-coefficient |
| Lysine | 6.51 | 1.55 |
| Histidine | 1.81 | 5.21 |
| Arginine | 3.67 | 2.24 |
| Aspartic acid | 9.82 | 0.79 |
| Threonine | 5.20 | 3.32 |
| Serine | 7.32 | 3.91 |
| Glutamic acid | 11.50 | 0.54 |
| Proline | 5.16 | 2.76 |
| Glycine | 6.97 | 1.71 |
| Alanine | 7.74 | 4.70 |
| Cystine/2 | 1.94 | 3.45 |
| Valine | 6.32 | 6.54 |
| Methionine | 2.43 | 4.54 |
| Isoleucine | 4.09 | 1.97 |
| Leucine | 9.46 | 2.63 |
| Tyrosine | 2.96 | 8.88 |
| Phenylalanine | 5.44 | 1.13 |
| Tryptophan | 1.69 | 7.04 |

The following properties of $PP_{10}$ were found which can be used for the isolation of the new tissue protein:

(1) $PP_{10}$ is precipitated with ammonium sulfate at pH 7.0 and a saturation of between 30–60% from aqueous solutions;

(2) $PP_{10}$ is precipitated with water-soluble acridine bases, for example 2-ethoxy-6,9-diaminoacridine lactate (Rivanol$^{(R)}$) at pH-values of between 7 and 9 and a concentration of 0.4 to 0.8% (w/v), however not or scarcely at pH 6.0, if the Rivanol concentration is 0.4%;

(3) When precipitated with ethanol, $PP_{10}$ remains in the supernatant in physiogical salt solutions at pH 7.0 up to a concentration of 25% of alcohol;

(4) in preparative electrophoresis, $PP_{10}$ migrates in the range of $\alpha_1$-globulins;

(5) in gel-filtration (Sephadex$^{(R)}$), $PP_{10}$ occurs in the range of proteins with molecular weights of 30 000 to 90 000;

(6) $PP_{10}$ can be adsorbed on weakly basic ion exchangers such as, for example DEAE-cellulose or DEAE-Sephadex at low conductivity (about 0–2 mS) and neutral or weakly alkaline pH-value (about pH 7 to 9);

(7) $PP_{10}$ can be enriched from its aqueous solution by immuno-adsorption and isolated.

The invention furthermore relates to processes for isolating $PP_{10}$ which comprise fractionating an aqueous extract of placentas, but also other aqueous solutions containing this protein, using and applying the above-described properties. Besides ammonium sulfate, it is evident that the neutral salts commonly used in biochemistry may be used for precipitating $PP_{10}$. In addition to acridine bases, water-soluble derivatives of a quinoline base, which are used in protein fractionations, may likewise be used.

Corresponding to its electrophoretic behavior and the molecular weight found according to the invention, even other measures for isolating the protein may be employed which enable the separation of an $\alpha_1$-globulin from other plasma- or tissue-proteins. With a view to the molecular weight, the various methods of gel-filtration, gel-chromatography or ultra-filtration may be used. This is also proved by the property of $PP_{10}$ of being able to be bound on weakly basic ion exchangers and of being eluted therefrom.

Isolation of the substance of the invention can be carried out by a selected combination of the above-mentioned measures, which lead, on the one hand to an enrichment of $PP_{10}$, and on the other hand to a separation of this protein from other tissue proteins or plasma proteins. Accordingly, the object of the invention comprises the individual steps for enriching $PP_{10}$ and in the processes and measures used by combining the different processes for purifying $PP_{10}$.

The process for enriching $PP_{10}$ is characterized by the use of at least one of the measures 1 to 7 or of their chemical or biochemical preparative equivalents.

$PP_{10}$ has antigenic properties; if animals are immunized with this protein, specific antibodies are formed. The detection and the determination of $PP_{10}$ by immunological methods has diagnostic significance on the one hand for control of pregnancies, on the other hand for the detection especially of trophoblastic tumors, but also of non-trophoblastic tumors, as well as for the control of the course of the disease and for the control of the therapy of such diseases.

The following Example illustrates the invention:

EXAMPLE

(A) Extraction of the placentas and fractionation of the extract with Rivanol and ammonium sulfate 1000 kg of deep-frozen human placentas were comminuted in a cutting mixer and extracted with 1000 l of a 0.4% (w/v) NaCl-solution. After separation of the tissue residue by centrifugation, the extract was adjusted to pH 6.0 with 20% (w/w) acetic acid and combined, under stirring, with 200 l of a 3% (w/v) solution of 2-ethoxy-6,9-diaminoacridine-lactate (Rivanol(R) Hoechst AG). The precipitate formed was removed by centrifugation and rejected. The supernatant was combined with 1% w/v of Bentonite A (Messrs. Erbsloh and Co., Geisenheim/Rhein), the pH-value was adjusted to 7.0 by the addition of 2N NaOH and filtered. The filtrate was combined slowly, while stirring, with 30% w/v of ammonium sulfate; thereupon the placenta protein $PP_{10}$ precipitated together with other proteins. The precipitate was filtered off, whereupon about 12 kg of a moist past were obtained, hereinafter designated as fraction A. On the average, 500 g of this paste contained about 250 mg of $PP_{10}$.

(B) Gel-filtration on Sephadex G-150

500 g of fraction A were dissolved in about 400 ml of water and dialyzed against a 0.1 M Tris-HCl-buffer (pH 8.0), containing 1.0 Mole/l NaCl and 0.1% of $NaN_3$ (buffer solution I). The protein-containing solution was applied to a column filled with Sephadex G-150 (20×100 cm) and subjected to gel-filtration. For the elution, buffer solution I was used. The eluates were tested by the gel diffusion test according to Ouchterlony with a specific anti-$PP_{10}$ rabbit serum; all fractions containing the placenta-specific protein $PP_{10}$ were collected and concentrated on an ultrafilter (Amicon UF 2000) using PM-10 membranes to about 300 ml. This solution (fraction B) contained a total of about 100 mg of $PP_{10}$.

(C) Enrichment of $PP_{10}$ by immuno-adsorption

1. Preparation of the immuno-adsorbent: 470 ml of an anti-$PP_{10}$-serum from rabbit were dialyzed against a 0.02 M phosphate buffer (pH 7.0) and chromatographed on DEAE-cellulose in order to separate the immunoglobulins. The immunoglobulin fraction (3.23 g of protein) was then reacted with 323 g of especially purified agarose in spherical form (Sepharose (R) 4 B of Messrs. Pharmacia, Uppsala, Sweden) which had been activated with 40.5 g of cyanogen bromide and thus bound covalently to a carrier.

The process is described by Axen, R., Porath, J., Ernbach A., Nature, 214, page 1302 (1967).

With the immuno-adsorbent prepared in this manner, the placenta-protein $PP_{10}$ could be isolated from its solution, especially from $PP_{10}$-enriched placenta-extract fractions.

2. Carrying out the immunoadsorption.

The immuno-adsorbent was suspended in buffer solution I (0.1 M Tris-HCl-buffer, pH 8.0, with 1.0 Mole/l of NaCl and 0.1% of $NaN_3$), then introduced into a column for chromatography (5.5×20 cm) and washed with buffer solution I. Then, 60 ml of the $PP_{10}$-containing solution (fraction B) were allowed to slowly migrate through the column, whereby the $PP_{10}$ was bound immuno-adsorptively. The column was washed thoroughly with buffer I and the adsorbed protein was then eluted with about 600 ml of a 3 M potassium thiocyanate solution. The $PP_{10}$-containing eluates were dialyzed against buffer solution I and concentrated in the ultrafilter to about 15 ml. Yield per adsorption: 6–7 mg of $PP_{10}$.

Directly after the elution of $PP_{10}$, the adsorbent in the column was neutralized with buffer solution I and washed thoroughly; it could then be used again for the adsorptive fixation of $PP_{10}$.

(D) High purification of $PP_{10}$

The protein isolated by immuno-adsorption is often contaminated by unspecifically bound serum proteins and other placenta tissue proteins. Separation of the main quantity of the accompanying serum proteins can be effected, for example, by gel-filtration on Sephadex G-150 or by impurities chromatography on DEAE-cellulose. The other remaining impurities are then removed by inverse or negative immuno-adsorption, i.e. with the aid of carrier-bound antibodies against the proteins still present as contamination.

What is claimed is:

1. An isolated, concentrated tissue protein, $PP_{10}$, obtained by fractionating a placental extract or an aqueous solution obtained from such an extract, said tissue protein having:

(a) a protein proportion of 93±3%;
(b) an amino acid analysis of

|  | mol % | Variation Coefficient (%) |
|---|---|---|
| lysine | 6.51 | 1.55 |
| histidine | 1.81 | 5.21 |
| arginine | 3.67 | 2.24 |
| aspartic acid | 9.82 | 0.79 |
| threonine | 5.20 | 3.32 |
| serine | 7.32 | 3.91 |

-continued

| | mol % | Variation Coefficient (%) |
|---|---|---|
| glutamic acid | 11.50 | 0.54 |
| proline | 5.16 | 2.76 |
| glycine | 6.97 | 1.71 |
| alanine | 7.74 | 4.70 |
| cystine/2 | 1.94 | 3.45 |
| valine | 6.32 | 6.54 |
| methionine | 2.43 | 4.54 |
| isoleucine | 4.09 | 1.97 |
| leucine | 9.46 | 2.63 |
| tyrosine | 2.96 | 8.88 |
| phenylalanine | 5.44 | 1.13 |
| tryptophan | 1.69 | 7.04 |

(c) a carbohydrate proportion of 6.65±1.55%, consisting of 4.8±1.0% of hexoses, 1.2±0.3% of hexosamine, 0.05±0.05% of fucose, and 0.6±0.2% of sialic acid;

(d) a sedimentation coefficient $S_{20/w}^0$, of 3.8±0.2 S;

(e) a molecular weight determined in the ultracentrifuge of 48,000±5,000;

(f) a molecular weight determined in sodium dodecylsulfate-containing polyacrylamide gel of 65,000±5,000;

(g) an extinction coefficient $E_1{}_{cm}^{1\%}$ (280 nm) of 10.9±0.5;

(h) an electrophoretic mobility in the range of the α1-globulins; and (i) an isoelectric point of 5.1±0.3.

2. A tissue protein, PP10, as in claim 1 obtained by fractionating an extract of human placentas.

3. An antiserum to the tissue protein of claim 1 obtained by injecting said tissue protein into an animal, taking the blood of the animal after some time, and recovering the serum from said blood.

* * * * *